United States Patent [19]

King et al.

[11] Patent Number: 4,962,755
[45] Date of Patent: Oct. 16, 1990

[54] METHOD FOR PERFORMING ENDARTERECTOMY

[75] Inventors: Robert M. King, Minneapolis; H. David Dalquist, Edina, both of Minn.

[73] Assignee: Heart Tech of Minnesota, Inc., St. Louis Park, Minn.

[21] Appl. No.: 382,918

[22] Filed: Jul. 21, 1989

[51] Int. Cl.[5] ............................................. A61B 17/22
[52] U.S. Cl. ..................................... 128/24 A; 604/22
[58] Field of Search ................. 128/24 AA, 24 AE; 604/22, 28; 606/127, 128

[56] References Cited

U.S. PATENT DOCUMENTS

| | | | |
|---|---|---|---|
| 3,352,303 | 11/1967 | Delaney | 604/22 |
| 3,368,280 | 2/1968 | Friedman et al. | 32/58 |
| 3,433,226 | 3/1969 | Boyd | 128/24 AA |
| 3,510,476 | 3/1971 | Gregg | 128/24 AA |
| 4,169,984 | 10/1979 | Parisi | 310/323 |
| 4,223,676 | 9/1980 | Wunchinich et al. | 128/276 |
| 4,883,458 | 11/1989 | Shiber | 604/22 |

*Primary Examiner*—Kyle L. Howell
*Assistant Examiner*—Kevin Pontius
*Attorney, Agent, or Firm*—Haugen and Nikolai

[57] ABSTRACT

A method of performing an endarterectomy comprising the steps of exposing the blood vessel containing the atheroma to be excised, next forming an incision through the wall of the blood vessel at a location subtended by the atheroma, then inserting a probe through the incision and imparting ultrasonic vibrations to the probe while manipulating the probe relative to the atheroma to loosen the atheroma from the surrounding blood vessel and extracting the loosened atheroma through the incision. The further step of injecting a sterile liquid over the probe during its vibration has been found to enhance the ability of the probe to loosen the atheroma.

7 Claims, 2 Drawing Sheets

METHOD FOR PERFORMING ENDARTERECTOMY

BACKGROUND OF THE INVENTION

I. Field of the Invention

This invention relates generally to a surgical procedure for treating an obstructed blood vessel and more particularly to a novel method of performing an endarterectomy in which ultrasonic energy is applied between the adventitia and the obstructing atheroma to facilitate the loosening thereof.

II. Description of the Prior Art

In treating atherosclerosis, one accepted method is the surgical excision of the atheroma from the interior wall of the affected blood vessel through an incision made into the blood vessel (arteriotomy) at the site of the lesion. The procedure is generally referred to as an endarterectomy.

A variety of surgical implements have been developed for facilitating this procedure. In this regard, reference is made to the Curi U.S. Pat. No. 3,939,138; Fogarty U.S. Pat. No. 4,287,890; Fogarty U.S. Pat. No. 4,621,636, Chiulli U.S. Pat. No. 4,038,985, Chin U.S. Pat. No. 4,559,927 and Chin U.S. Pat. No. 4,574,781. The use of these implements have met with varying degree of success in removing stenotic lesions.

It is important that when the lesion is loosened from the adventitia that it remains intact and that small particles thereof do not break loose and float to a location where an occlusion may result in serious ischemia. For example, in performing an endarterectomy on a coronary blood vessel, a blockage may result in a life-threatening infarct. When a carotid artery is involved, a small fragment of the lesion may embolize float to a tiny blood vessel in the brain precipitating a stroke or death. Moreover, the endarterectomy procedure can only be performed by surgeons of significant knowledge and utmost skill.

OBJECTS

It is accordingly a principal object of the present invention to provide an improved method of performing an endarterectomy.

Another object of the invention is to provide a method of performing an endarterectomy in which the atheroma may be more readily separated from the wall of the affected blood vessel Yet another object of the invention is to provide an improved method of performing an endarterectomy in which the proximal and distal portions of the plaque deposit may be removed intact.

A still further object of the invention is to provide an improved method of performing an endarterectomy in which an ultrasonically vibrated scalpel or probe is used as the plaque-separating instrument.

A yet further object of the invention is to provide an improved method of conducting an endarterectomy wherein a hand-held, ultrasonically vibrated probe is flooded with a sterile saline as the probe is used to separate the plaque deposit from the surrounding vessel tissue.

SUMMARY OF THE INVENTION

The present invention involves an improved method of performing an endarterectomy, greatly increasing the probability that the plaque will be removed intact without fragmentation. The blood vessel containing the stenotic plaque is first surgically exposed and a longitudinal incision (arteriotomy) performed proximal to the atheroma to be removed. An ultrasonically vibrated probe is then inserted through the incision and manipulated around the interface between the adventitia and the atheroma. The simultaneous injection of a sterile saline over and about the probe as it is vibrated and manipulated is found to enhance the loosening of the lesion as a unitary piece. Once loosened, it may readily be removed using a forcep or similar implement. Once removed, the arteriotomy is closed by suturing.

In carrying out the method, the probe may be attached to a laminated stack of magnetostrictive material contained in the handle. A high frequency voltage obtained from an ultrasonic generator is applied across the laminations causing them to be alternately attracted and repelled to vibrate the probe at the frequency of the applied voltage. A cooling liquid may be circulated over the lamination stack to maintain the handle at a desired low temperature. The probe itself may take on a variety of shapes and tip styles to facilitate the loosening of the atheroma.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
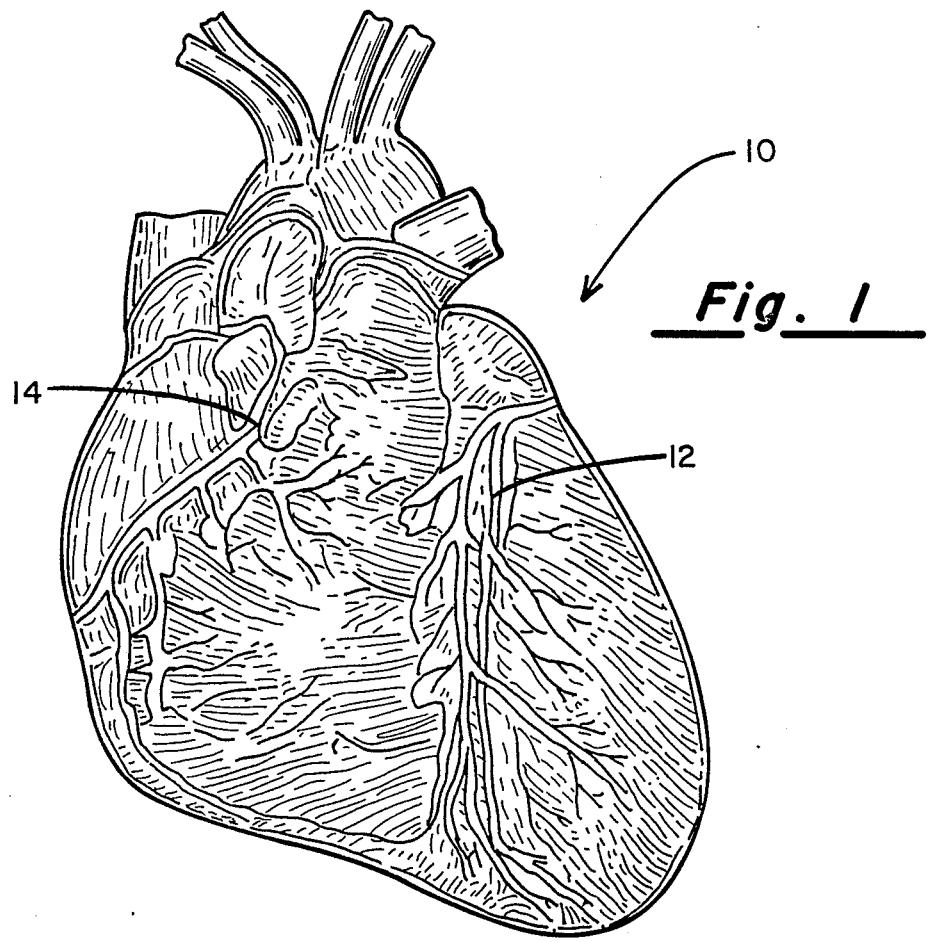
FIG. 1 is an anterior view of the human heart illustrating various ones of the coronary blood vessels.

As is pointed out in the introductory portion of this patent specification, an endarterectomy is a well accepted procedure for treating atherosclerosis. While the procedure may be utilized to clear atheromas from peripheral blood vessels, the method of the present invention will be explained in connection with the treatment of coronary artery disease. In this regard, there is shown identified by numeral 10 in FIG. 1, an anterior view of a human heart. Identified by numeral 14 is the right coronary artery while numeral 12 refers to the anterior interventricular branch of the left coronary artery. In patients suffering from coronary artery disease, the interior walls of these arteries may become involved with the buildup of fatty and calcified deposits which tend to stenose the lumen of the blood vessels, limiting the normal supply of blood to cardiac tissue distal of the buildup. Endarterectomy is a surgical procedure for alleviating this condition through surgical intervention and removal of the stenotic plaque.

Figure 2:
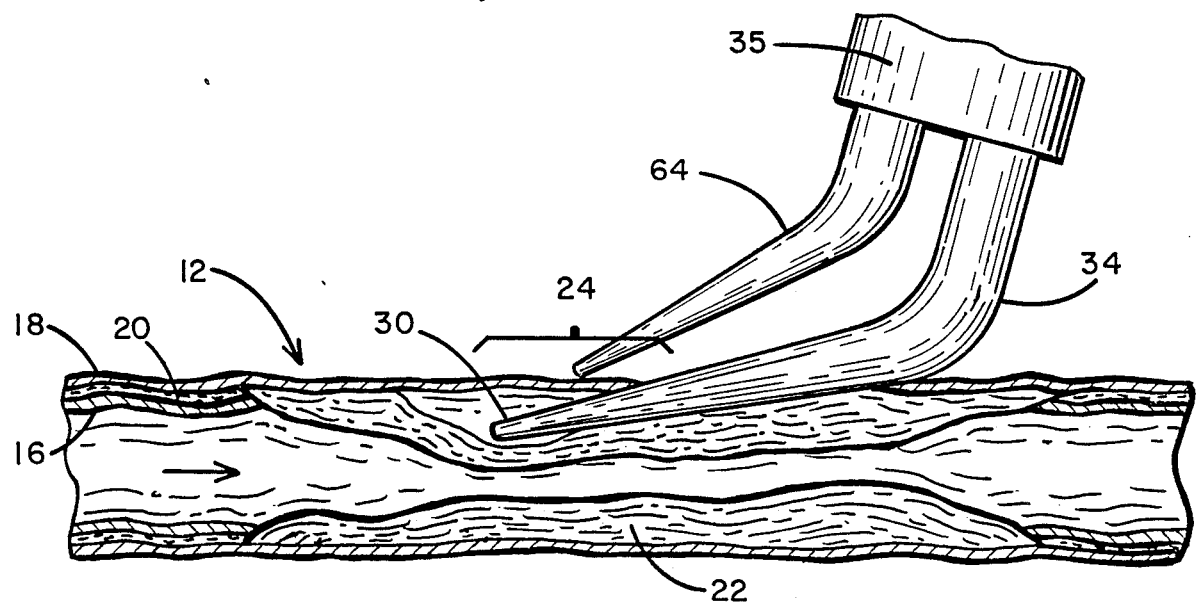
FIG. 2 is a greatly enlarged cross-sectional view of the right coronary artery identified in FIG. 1.

FIG. 2 is a greatly enlarged cross-sectional view of one of the coronary arteries 12 or 14 and, like all such tissue, includes an innermost lining of cells called the endothelium or intima 16 and an outer layer 18 called the adventitia. In between these two layers is a layer of circularly arranged smooth muscle fibers and connective tissue fibers referred to as the media and identified by numeral 20 in FIG. 2.

Shown disposed in the arterial segment of FIG. 2 is a stenotic lesion or atheroma 22 which has built up over a period of time within the blood vessel to the point where the flow of blood is greatly restricted. Moreover, the atheroma replaces the intima 16 and also commonly involves the media as well.

In carrying out an endarterectomy to excise the atheroma or stenotic lesion 22, a median sternotomy is first performed and an incision is made through the pericardium to expose the heart. Exterior fatty tissue surrounding the affected portion of the blood vessel is then cut away and a longitudinal incision approximately 1 cm long is made through the vessel wall (arteriotomy) approximately midway along the length of the lesion to be removed as at 24. Next, and in accordance with the present invention, a hand-held, ultrasonically vibrated probe 26 is introduced through the incision while a sterile saline solution is simultaneously injected to flood the distal end portion of the probe 26. The surgeon then precisely manipulates the probe between the atheroma 22 and the advantitia 18. It is found that the combination of the ultrasonic vibration of the probe and its interaction with the sterile saline enhances the clean separation of the atheroma 22 from the advantitia 18.

Once the portion of the plaque distal to the incision site 24 has been loosened, it is removed using a forceps. Following that, the same manipulation of the ultrasonically vibrating probe 26 is used to free the proximal portion of the plaque from its involvement with the blood vessel tissue. The atheroma is then removed through the arteriotomy site using a forceps.

Having earlier performed numerous endarterectomy operation, I have found that the use of an ultrasonically vibrating probe of the type described hereinbelow greatly facilitates the procedure. Specifically, I have found that the stenotic lesion tends to remain intact, allowing it to be removed as a unit through the endarterectomy incision site. Moreover, the instrument tends to be selective in establishing a clean interface between the lesion and the outermost layer of the blood vessel.

Once both the distal and proximal portions of the atheroma have been removed, the incision through the vessel wall is either sutured closed or a saphenous vein bypass graft placed.

Figure 3:
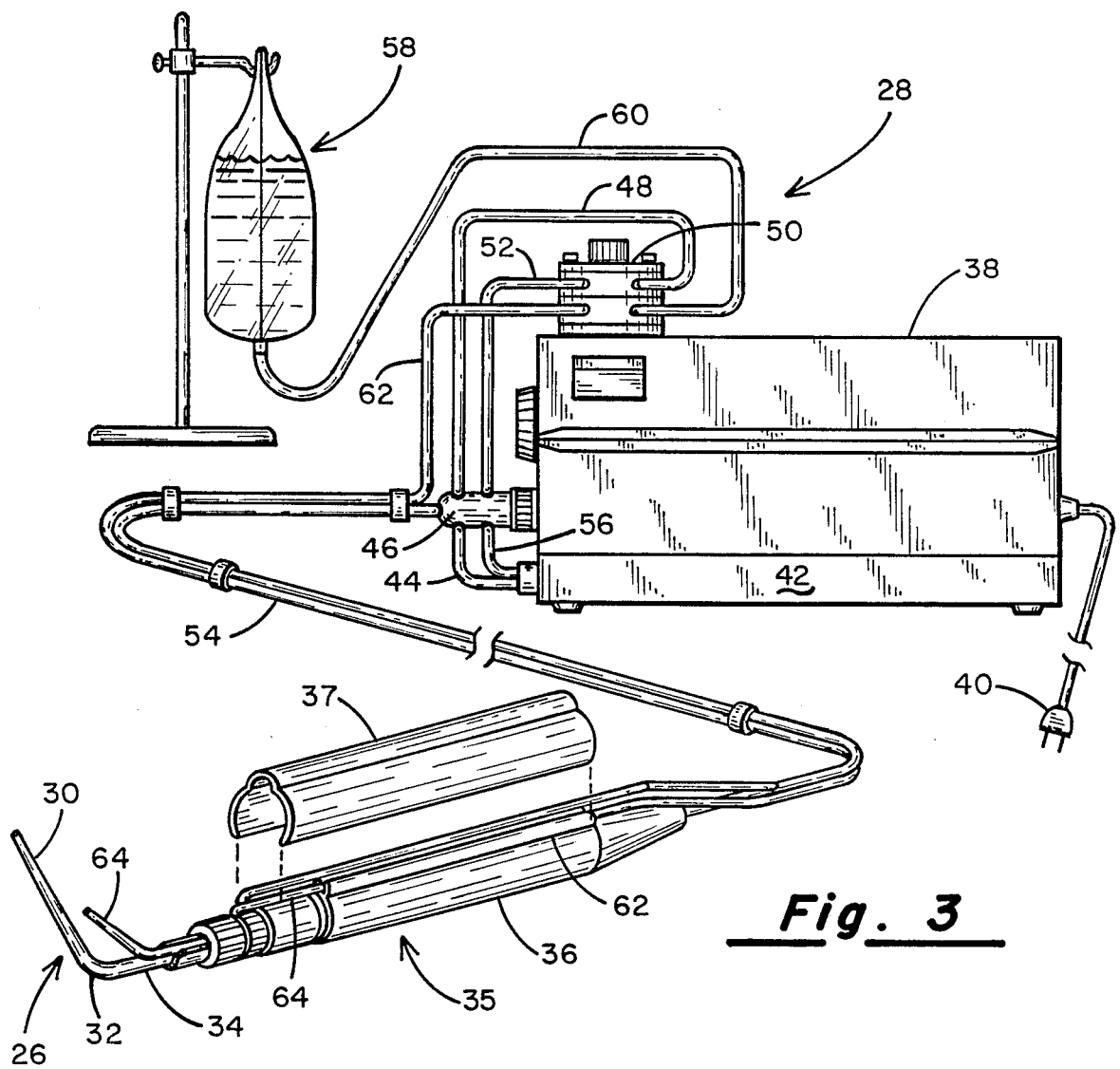
FIG. 3 is a pictorial view of the apparatus used in carrying the method of the present invention.

Referring next to FIG. 3, the apparatus utilized to perform the method of the present invention will be described. The assembly is referred to generally by numeral 28 and includes a hand-held probe assembly 26 comprising a flat spatula blade 30 which is bent at a predetermined obtuse angle as at 32 and includes a shank portion 34 which is welded to the laminated stack of the ultrasonic transducer contained within the handle housing 36.

The ultrasonic vibrator or transducer sold by Cavitron, Inc. preferably comprises a plurality of strips of a magnetostrictive material which are joined together at opposed ends thereof and which are concentrically disposed within the center of a helical coil. When the coil is energized by a high frequency generator, it causes the probe 26 to vibrate. Such a handpiece is disclosed in U.S. Pat. No. 4,063,557 which is assigned to the Cavitron Corporation of New York City.

To drive the handpiece 35, a signal generator such as of the type sold by Simplified Systems, Inc. of Miami Beach, Fla., under the trademark SONATRON ® may conveniently be utilized. The generator is identified by numeral 38 and is adapted to be connected by an electrical plug 40 to a source of 115 volt, 60 Hz current. It is capable of producing an output signal at 25,000 Hz at a power output in an operator-adjustable range of from 10–30 watts. The generator output is selectively actuated by a footswitch control (not shown) or, alternatively, by a push-button switch located on the probe handle 36 itself.

In that the application of the high frequency voltage to the coil and thence to the laminated stack results in a substantial heat rise in the transducer, it is found expedient to water cool the hand-held probe assembly. In this regard, a supply of cooling water may conveniently be located in a tank 42 upon which the generator 38 rests. Cooling water may be drawn from the tank 42, via tube 44, which joins to a manifold 46. A further tube 48 leads to the input of a parastaltic pump and the output of the pump is carried via tube 52 back to the manifold 46, and from there, through a double lumen flexible tube 54, to the interior of the handle housing 36. The return flow is through the second lumen in the tube 54, through the manifold 46 and, thence through tube 56, back to the tank 42. Given the volume of cooling water contained in the tank 42 and the relatively short time intervals that the ultrasonic transducer is being driven during the course of a endarterectomy procedure, the cooling capacity afforded is sufficient to maintain the handle and probe at a comfortable level.

It has also been determined to be effective to spray or flood the distal tip of the probe 30 with a liquid during the course of the surgical procedure. The utilization of a liquid in this fashion is believed to more effectively couple the ultrasonic energy to the tissue being excised and, thus, the surgical removal is enhanced. To achieve this desired end, a supply of sterile saline as at 58 is coupled via a tube 60 to the pulsatile pump 50 and the thus pressurized flow passes through flexible tubing 62 to a metal tube 64 located near the distal end of the handle, that tube being formed so as to spray the sterile saline over the distal end portion of the probe 30. The flow rate and pressure of the saline can be regulated by adjusting the speed of the motor portion of the pulsatile pump 50.

Figure 4A:
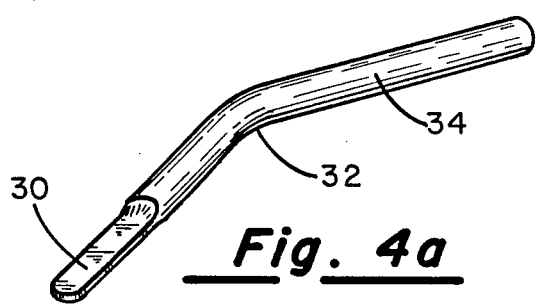
FIGS. 4a, 4b and 4c show a series of probe shapes used with the apparatus of the FIG. 3.
Figure 4C:
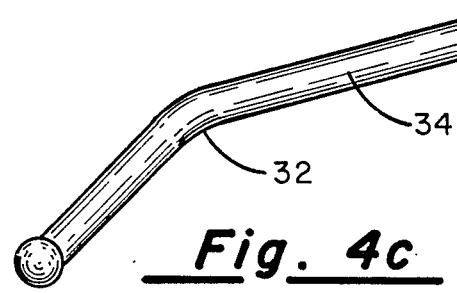
Figure 4B:
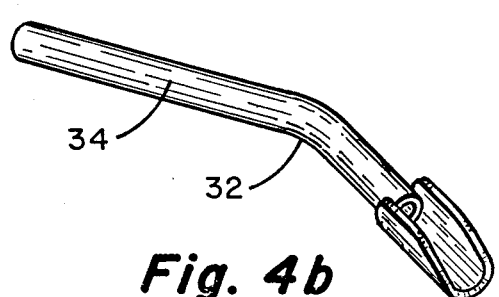

It has also been found that the efficacy of the ultrasonic probe in separating atheromas from surrounding vascular tissue is sometimes enhanced by the particular shape of the probe tip. In this regard, reference is made to FIGS. 4a, 4b and 4c. A flat tapered spatula blade has been determined to provide excellent results in small diameter vessels. In other instances, the inclusion of a tip which has an arcuate profile transverse to its longitudinal axis forming a spoon shaped tip on the end of the spatula (FIG. 4b) has proven efficacious in loosening plaque from the coronary arteries as the cardiac surgeon, in effect, traces a circular path with the curved tip as the tip is ultrasonically vibrated and simultaneously flooded with sterile saline. The tip illustrated in FIG. 4c includes a spherical ball at its tip and this implement has been found to be useful in treating stenotic lesions in larger peripheral blood vessels.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A method of removing atherosclerotic plaque deposits from the interior of a blood vessel comprising the steps of:
   (a) surgically exposing the segment of said blood vessel containing said plaque deposits;
   (b) forming an incision through the wall of the blood vessel at a location between the proximal and distal ends of said plaque deposit;
   (c) introducing an ultrasonically vibrated hand-held probe through said incision;
   (d) manipulating said probe relative to the interface between said plaque deposit and the involved wall of said blood vessel to free said plaque deposit from the blood vessel tissue;
   (e) sequentially removing the portions of said plaque located proximally and distally of said incision intact through said incision; and
   (f) closing said incision with sutures, or performing a distal bypass graft.

2. The method as in claim 1 and further including the step of injecting a sterile liquid about the distal end of said probe as said probe is being ultrasonically vibrated.

3. A method of removing atherosclerotic plaque deposits from the interior of a blood vessel comprising the steps of:
   (a) surgically exposing the segment of said blood vessel containing said plaque deposits;
   (b) forming an incision through the wall of the blood vessel at a location between the proximal and distal ends of said plaque deposit;
   introducing an ultrasonically vibrated hand-held needle probe through said incision;
   (d) manipulating said probe relative to the interface between said plaque deposit and the involved wall of said blood vessel to free said plaque deposit from the blood vessel tissue;
   (e) sequentially removing the portions of said plaque located proximally and distally of said incision intact through said incision; and
   (f) closing said incision with sutures, or performing a distal bypass graft.

4. A method of removing atherosclerotic plaque deposits from the interior of a blood vessel comprising the steps of:
   (a) surgically exposing the segment of said blood vessel containing said plaque deposits;
   (b) forming an incision through the wall of the blood vessel at a location between the proximal and distal ends of said plaque deposit;
   (c) introducing an ultrasonically vibrated hand-held needle probe through said incision, said probe is bent at a predetermined obtuse angle;
   (d) manipulating said probe relative to the interface between said plaque deposit and the involved wall of said blood vessel to free said plaque deposit from the blood vessel tissue;
   (e) sequentially removing the portions of said plaque located proximally and distally of said incision intact through said incision; and
   (f) closing said incision with sutures, or performing a distal bypass graft.

5. A method of removing atherosclerotic plaque deposits from the interior of a blood vessel comprising the steps of:
   (a) surgically exposing the segment of said blood vessel containing said plaque deposits;
   (b) forming an incision through the wall of the blood vessel at a location between the proximal and distal ends of said plaque deposit;
   (c) introducing an ultrasonically vibrated hand-held probe having a spoon-shaped distal end through said incision;
   (d) manipulation said probe relative to the interface between said plaque deposit and the involved wall of said blood vessel to free said plaque deposit from the blood vessel tissue;
   (e) sequentially removing the portions of said plaque located proximally and distally of said incision intact through said incision; and
   (f) closing said incision with sutures, or performing a distal bypass graft.

6. A method of removing atherosclerotic plaque deposits from the interior of a blood vessel comprising the steps of:
   (a) surgically exposing the segment of said blood vessel containing said plaque deposits;
   (b) forming an incision through the wall of the blood vessel at a location between the proximal and distal ends of said plaque deposit;
   (c) introducing an ultrasonically vibrated hand-held probe having a spherical tip thereon through said incision;
   (d) manipulating said probe relative to the interface between said plaque deposit and the involved wall of said blood vessel to free said plaque deposit from the blood vessel tissue;
   (e) sequentially removing the portions of said plaque located proximally and distally of said incision intact through said incision; and
   (f) closing said incision with sutures, or performing a distal bypass graft.

7. A method of removing atherosclerotic plaque deposits from the interior of a blood vessel comprising the steps of:
   (a) surgically exposing the segment of said blood vessel containing said plaque deposits;
   (b) forming an incision through the wall of the blood vessel at a location between the proximal and distal ends of said plaque deposits;
   (c) introducing an ultrasonically vibrated hand-held probe through said incision where said probe includes an elongated shaft of generally circular cross-section with a proximal end and a distal end, said shaft being bent at a predetermined obtuse angle at a location intermediate said proximal and distal ends and terminating in a flattened and tapered segment;
   (d) manipulating said probe relative to the interface between said plaque deposit and the involved wall of said blood vessel to free said plaque deposit from the blood vessel tissue;
   (e) sequentially removing the portions of said plaque located proximally and distally of said incision intact through said incision; and
   (f) closing said incision with sutures, or performing a distal bypass graft.

* * * * *